United States Patent
Roth et al.

(10) Patent No.: US 8,008,059 B1
(45) Date of Patent: Aug. 30, 2011

(54) METHOD UTILIZING ENZYME SUBSTRATES PRODUCING INSOLUBLE FLUORESCENT PRODUCTS AND CHROMOGENS, AND USE IN COMBINATION WITH ENZYME SUBSTRATES PRODUCING SOLUBLE PRODUCTS

(75) Inventors: Geoffrey N. Roth, Goshen, IN (US); Jonathan N. Roth, Goshen, IN (US)

(73) Assignee: Micrology Laboratories, LLC, Goshen, IN (US)

( * ) Notice: Subject to any disclaimer, the term of this patent is extended or adjusted under 35 U.S.C. 154(b) by 1164 days.

(21) Appl. No.: 11/725,088

(22) Filed: Mar. 16, 2007

Related U.S. Application Data (60) Provisional application No. 60/784,068, filed on Mar. 17, 2006.

(51) Int. Cl.
| | |
|---|---|
| C12N 1/00 | (2006.01) |
| C12N 1/20 | (2006.01) |
| C12N 1/10 | (2006.01) |
| C12N 1/12 | (2006.01) |
| C12N 1/16 | (2006.01) |
| C12Q 1/04 | (2006.01) |
| C12Q 1/02 | (2006.01) |
| C12N 9/14 | (2006.01) |
| C12N 9/52 | (2006.01) |
| C12N 9/60 | (2006.01) |

(52) U.S. Cl. ............ 435/243; 435/29; 435/42; 435/195; 435/220; 435/224; 435/252.1; 435/254.2; 435/258.1; 435/966

(58) Field of Classification Search .................... 435/29, 435/42, 195, 220, 224, 243, 252.1, 254.2, 435/258.1, 966
See application file for complete search history.

(56) References Cited

U.S. PATENT DOCUMENTS

| | | | |
|---|---|---|---|
| 4,923,804 A | 5/1990 | Ley et al. | |
| 5,210,022 A | 5/1993 | Roth et al. | |
| 5,358,854 A | 10/1994 | Ferguson | |
| 5,393,662 A * | 2/1995 | Roth et al. | 435/38 |
| 5,552,288 A * | 9/1996 | Christensen et al. | 435/7.9 |
| 6,063,590 A | 5/2000 | Brenner et al. | |
| 6,306,621 B1 | 10/2001 | Brenner et al. | |
| 6,350,588 B1 | 2/2002 | Roth et al. | |
| 6,670,145 B2 | 12/2003 | Brenner et al. | |
| 6,787,332 B2 | 9/2004 | Roth et al. | |
| 7,273,719 B2 | 9/2007 | Roth et al. | |
| 7,344,854 B2 | 3/2008 | Roth et al. | |

OTHER PUBLICATIONS

Heizmann, et al. 1988. Rapid Identification of *Escherichia coli* by Fluorocult Media and Positive Indole Reaction. Journal of Clinical Microbiology, vol. 26, pp. 2682-2684.*

Manafi M. and Rotter, M.L. 1991. A new plate medium for rapid presumptive identification and differentiation of Enterobacteriaceae. INternational Journal of Food Microbiology. Nov. 1991,vol. 14, No. 2, pp. 127-134.

Manafi, M. Kneifel, W.1991. Fluorogenic and chromogenic substrates-a promising tool in microbiology. Acta Microbiol. Hung., vol. 38, Nos. 3-4, pp. 293-304.

* cited by examiner

*Primary Examiner* — Jon P Weber
*Assistant Examiner* — Kailash Srivastava
(74) *Attorney, Agent, or Firm* — Botkin & Hall, LLP (57) ABSTRACT

A method of detection of cells, microorganisms, or molecules by the use of various combinations of fluorogens and a chromogens which yield fluorophores and chromophores when cleaved by specific enzymes and which can be viewed by UV and visible light. Included is the method of application of a family of compounds producing both insoluble fluorophores and chromophores identified as dual enzyme substrates.

12 Claims, 6 Drawing Sheets
(5 of 6 Drawing Sheet(s) Filed in Color)

FIG.1

PHOTO 1

PHOTO 2

PHOTO 3

PHOTO 4

PHOTO 5

PHOTO 6

PHOTO 7

PHOTO 8

PHOTO 9

METHOD UTILIZING ENZYME SUBSTRATES PRODUCING INSOLUBLE FLUORESCENT PRODUCTS AND CHROMOGENS, AND USE IN COMBINATION WITH ENZYME SUBSTRATES PRODUCING SOLUBLE PRODUCTS

CROSS REFERENCE TO RELATED APPLICATION

This application claims the benefit of U.S. Provisional Application No. 60/784,068 filed Mar. 17, 2006, the disclosure of which is hereby incorporated by reference.

BACKGROUND OF THE INVENTION

Current microbial tests are qualitative which pose definite problems. Two notable problems are the slowness of achieving results, and the high cost and availability of certain reagents used in various test formulations.

In recent years, the use of chromogenic, fluorogenic and non-chromogenic enzyme indicators has come into increasing use due to ease of use and rapid detection, especially in the field of microbiology. Edberg patented (U.S. Pat. No. 4,925,789) the use of one soluble fluorogen (methyumbelliferone-fluorescent blue) for detection of beta-galactosidase and one soluble chromogen (nitrophenol-yellow) for the detection of beta glucuronidase. This test is in a broth. However, literature (see Brenner U.S. Pat. Nos. 6,063,590; 6,306,621; and 6,670,145) has taught that fluorogens and chromogens which yield soluble products are not good for use on traditional agar or other gel type plate tests or for membrane filtration tests because the soluble indicator does not stay with the microbial colony making it easy to detect, but spreads out across the plate so one can not tell what it is (or is not) supposed to indicate. One answer to this problem came with the discovery that indolyl substrates, especially halogenated indolyl substrates, can be enzymatically cleaved to produce insoluble colors that will stay with a microbial colony, and make its detection simple. Ley (U.S. Pat. No. 4,923,804) took advantage of this idea and patented the use of indolyl beta glucuronidase to detect *E. coli* with membrane filtration. Roth (U.S. Pat. No. 5,210,022) was the first to use two colors of insoluble chromogens to detect two different enzymes at once, and put it into practice. Ferguson (U.S. Pat. No. 5,358,854) synthesized the novel chloroindolyl galactoside for Roth to detect coliforms, and Roth combined this with bromo-chloro-glucuronide to detect and differentiate *E. coli* and other coliforms simultaneously. Another proposed approach used a soluble fluorogen and an insoluble chromogen, but the use of soluble fluorogenic and/or chromogenic substrates in a solid gel or membrane filtration test has been seen as undesirable, again, due to the diffusible nature of their products (see Brenner patents).

SUMMARY OF THE INVENTION

This invention relates in at least in part to microbial testing and will have application in the detection of such items as organisms through the use of fluorogenic or chromogenic enzyme substrates.

One embodiment makes use of an absorbent pad as a base onto which at one side a diagnostic material of at least one of a fluorogenic, chromogenic or nonchromogenic quality is placed. A sample which contains a specific target item, such as an organism, is applied to the diagnostic material to cause upon incubation an enzyme to be absorbed at least in part through the pad. UV light and visible light are used to view both sides of the pad to detect the fluorescent and chromogenic appearances representing the target item.

In another embodiment, the diagnostic material provides both a fluorophore and chromophore appearance at one side of the base.

Accordingly, it is an object of this invention to provide a method of detecting specific organisms in rapid fashion.

Another object of this invention is to provide a method of microbial testing which is economical and provides accurate results.

Other objects will become apparent upon a reading of the following description.

BRIEF DESCRIPTION OF THE DRAWINGS

The patent or application file contains at least one drawing/photograph executed in color. Copies of this patent or published patent application with color drawing(s)/photograph(s) will be provided by the Office upon request and payment of the necessary fee.

Photo 1 shows colonies growing on the upper surface of the filter.

Photo 2 shows the colonies in Photo 1 as viewed in UV light.

Photo 3 shows the colonies in Photo 1 as viewed from the bottom of the filter.

Photo 4 shows six different bacteria species on the filter.

Photo 5 shows the bacteria in Photo 4 as seen under a UV light.

Photo 6 shows the bacteria in Photo 4 as viewed from the bottom of the filter.

Photo 7 shows the bacteria in Photo 4 subjected to a fluorescence enzyme.

Photo 8 shows the bacteria in Photo 7 as viewed in UV light; and

Photo 9 shows the bacteria in Photo 7 as viewed from the bottom of the filter.

DETAILED DESCRIPTION OF INVENTION

It has proven to be beneficial in certain item testing, such as for bacteria, to use a fluorogen or chromogen yielding a soluble fluorophore or chromophore when cleaved by its specific enzyme. This is best done on a solid surface test if the petri dish or container has a very thin absorbent pad, used as a base, laid inside against the bottom of the dish under the gel or holding the test broth. As soon as the test is initiated, and the microbe begins to produce the enzymes, they break down the fluorogenic, chromogenic, and/or nonchromogenic substrates to release the soluble products, which immediately begin to move down through the absorbent pad, where they can be detected very quickly.

The thinness of the absorbent pad is crucial with regard to speed as a thinner pad minimizes the time of diffusion of the fluorophore or chromophore from the point of production through the filter as it makes its way through the absorbent pad to the point where it can be readily observed as a distinct spot on the pad underside as quickly as possible. Regardless of the type of pad used, it is important that the results are read by counting the spots (representing soluble fluorogen or chromogen) present on the underside of the pad.

Thinner pads may also be less expensive than regular-sized pads. In any case, the type, as distinguished from its thickness, of pad used (except for toxicity concerns) has never been an issue in the literature. Currently, a standard thick-type pad is universally used for all membrane filtration. Pads are rarely, if ever, used in agar and gel tests currently. It is suggested that a pad thickness between 400 and 1000 micrometers will provide a suitable test in a reasonably fast time period.

The observation of the soluble target material (fluorophore or chromophore) by viewing the underside of the pad is particularly important when more than one fluorogen or chromogen is used in the test medium. This is true because it was recently discovered that different fluorogenic/chromogenic enzyme substrates possess different properties. For example, generally fluorogenic enzyme substrates produce only a soluble fluorogenic product (fluorophore) when acted upon by their specific enzyme, and generally chromogenic enzyme substrates produce only a chromogenic product (chromophore) when acted upon by their specific enzyme. However, previously undescribed properties in which a single enzyme substrate exhibits the production of both a fluorogenic product and a chromogenic product when acted upon by its specific enzyme are herein disclosed and characterized as dual enzyme substrates.

Interestingly, the fluorogenic product of these dual enzyme substrates is insoluble. That is, it does not diffuse out and away from the entity which causes its production, but is retained within that entity. This property gives it characteristics, distinctiveness and capabilities that are very different from the previously known soluble fluorophores that have been used in diagnostic testing. For example, a classic fluorogen such as 4-methylumbelliferyl-B-D-glucuronide (MU-gluc) may be combined with a dual enzyme substrate such as 6-chloro-3-indolyl-beta-D-galactoside (Red Gal®) in a single medium to test for the presence of two types of cells, one type being MU-gluc positive and the other galactoside (Gal) positive. In this situation, any MU-gluc positive cells will produce the soluble fluorescent MU product which can be seen and counted on the pad underside, while the Gal positive cells will produce an insoluble fluorescence which is visible only from the filter surface where the cell colonies are growing.

Thus, this invention relates in part to the detection of items, such as organisms, through the use of fluorogenic or chromogenic enzyme substrates which, upon exposure of the target material, experiences enzymatic cleavage to produce a fluorescent product (fluorophore) or chromogenic product (chromophore) that is drawn through an underlying absorbent pad where, at the underside of the pad, it can be visually identified such as by exposure to UV light, if needed.

There are many types of diagnostic tests for which this novel method can be used. For example, to take advantage of speed and economics, if one is testing for *E. coli*, the simplest test would involve the use of any size petri dish or container with a base which in this case is only a thin absorbent pad covering the bottom with a pourable mixture that will gel. A normal thickness pad will work if test speed is not crucial, but if rapid results are desired, a thin pad should be used. Fluorogenic enzyme substrate with additional nutrients are poured on top of the pad. For example, the pad could be soaked with a solution containing either 4-methylumbelliferyl-beta-glucuronide or 4-methylumbelliferyl-beta-D-galactoside (MUG) (50-100 micrograms/mL) or MUG with various nutrients, for example, casein or yeast extracts. After the test sample is filtered and placed onto the nutrient-soaked pad (the nutrient may be MUG alone), the petri dish is incubated until fluorescent spot(s) can be seen with the aid of UV light through the bottom of the petri dish.

Photograph 1 is a picture of the petri dish with several colored colonies. Photograph 2 is a picture of the colonies under UV. Notice fluorescence of both *E. coli* and non *E. coli* colonies. Photograph 3 is a picture of the bottom of the dish, showing the true *E. coli* spots from the corresponding colonies. False readings are essentially eliminated. Detectors that release insoluble chromogens and fluorogens of different colors for the same or different enzymes may also be incorporated, and these would be read from the top of the petri dish. Di-beta-glucuronide fluoroscein, and/or trifloromethylumbelliferyl-beta-glucuronide, and/or any coumarin based fluorogenic enzyme detector can be used instead of or with MUG to intensify and quicken the test, and/or change the fluorescent color.

Following is information to accompany a series of photos illustrating the principles and results of the material presented in the text.

Photo 1 shows 18 hour growth of *E. coli* (blue colonies) and non-*E. coli* bacteria (pink colonies) growing on the surface of a micropore membrane filter resting on an absorbent pad soaked with the liquid Coliscan® MF growth medium which contains the fluorogenic enzyme substrate 4-methylumbelliferyl-beta-D-glucuronide (MUG gluc).

Photo 2 shows the same plate and same view as shown in Photo 1, but as seen under direct long wave UV light in a dark room. It is to be noted that the colonies match in position and number on the plate. It should also be noted that virtually all the colonies are fluorescent and that the *E. coli* colonies exhibit a slight "fuzziness" around the edges due to the diffusion of the soluble fluorophore from the MUG gluc. The other colonies exhibit sharper borders due to the fact that the fluorophores coloring them are retained within the cells or are intracellular.

Photo 3 is the same plate as seen in Photos 2 and 3, but the plate is turned over and viewed from the bottom so the bright fluorescent spots representing the *E. coli* are shown as a mirror image of the pattern of the first two photos. Note the fluorescence of the non-*E. coli* is not seen, as it did not diffuse from the colonies downward into the pad.

Photo 4 shows eight hour growth of six different species of bacteria spotted on the surface of a micropore membrane filter resting on an absorbent pad soaked with the liquid growth medium sold under the name of Coliscan® MF and manufactured by Micrology Laboratories of Goshen, Ind., which does not contain MUG gluc. Therefore, no previously known fluorogenic substrate is in this medium. The organisms are: A) *E. coli* (6 o'clock); B) *Citrobacter freundii* (8 o'clock); C) *Klebsiella pneumoniae* (10 o'clock); D) *Enterobacter aerogenes* (12 o'clock);

E) *Salmonella typhimurium* (2 o'clock); and F) *Aeromonas hydrophila* (4 o'clock).

Photo 5 is the same plate and same view as shown in Photo 4, but as seen under direct long wave UV light in a dark room. Note that A, B, C and D all exhibit bright blue fluorescence. This fluorescence is present despite the fact that no previously known fluorogenic enzyme substrate was in the growth medium formula.

Photo 6 is the same plate as seen in Photos 4 and 5, but the plate is turned over and viewed from the bottom so it is obvious that the fluorescence present in the cultures when viewed from the top is absent. This is an indication that the fluorescence is intracellular (insoluble) and did not diffuse downward into the pad soaked with the growth medium.

Photo 7 shows eight hour growth of the same six species, in the same positions on the filter, of bacteria as shown in Photo 4, but in this case the absorbent pad is soaked with a liquid medium sold under the name ECA Check® and manufactured by Micrology Laboratories of Goshen, Ind., which contains the fluorogenic enzyme substrate MUG gluc.

Photo 8 is the same plate and same view as shown in Photo 7, but as seen under direct long wave UV light in a dark room. Note that A, B, C, D and F all show fluorescence in this top view. The question is whether the fluorescence is due to the MUG gluc or some other factor. This question is resolved in Photo 9.

Photo 9 is the same plate as 7 and 8, but the plate is turned over and viewed from the bottom so it is obvious that any fluorescence observed is from the soluble fluorophore of MUG gluc. In this case, only A (*E. coli*) is showing fluorescence, which is correct. None of the other bacterial species should exhibit fluorescence. This demonstrates that under test conditions B, C, D and F would have been considered as positive for glueuronidase if viewed from the top, as standard protocol dictates. Such a consideration would have been an error.

In any of the above examples, or in another test, any combination of enzyme(s) substrates, enzymes, or bacterial genera may be used or tested to achieve identification or differentiation. For example, fluorogenics (based on derivatives of coumarin such as methylumbelliferone or trifloromethylumbellferone, or fluoroscein, or resorufin or rezasurin, fluorescent tetrazolium salts, carboxy fluoroscein, carboxy rhodamine, tetramethylrhodamine, carboxymethylumbelliferone, or other nontoxic fluorogen molecules), chromogenics (indoxyl enzyme substrates, nitrophenyl substrates, soluble aminonaphtyl or alpha napthol substrates, phenolpthalein substrates, salicin, esculin, visible tetrazolium salts or other nontoxic chromogen molecules), and any combination of enzyme(s) such as glycosidases, peptidases, aminopeptidases, oxidases, phosphatases, sulfatases, DNAases, RNAases, gyrases, topoisomerases, phosphoglycosidases, arylphosphatases, arylsulfatases, hemolysins, tryptophanase, coagulases, amino acid metabolizing enzymes, esterases, etherases, decarboxylases, deaminases, aminases, amidases, peroxidases, lipases, arylamidases, caprylases, and any other microbial enzymes that can be chromogenically or fluorogenically or nonchromogenically detected, indicating any combination of microbes may be used, such as any genus or genera of bacteria or fungi.

Figure 1:
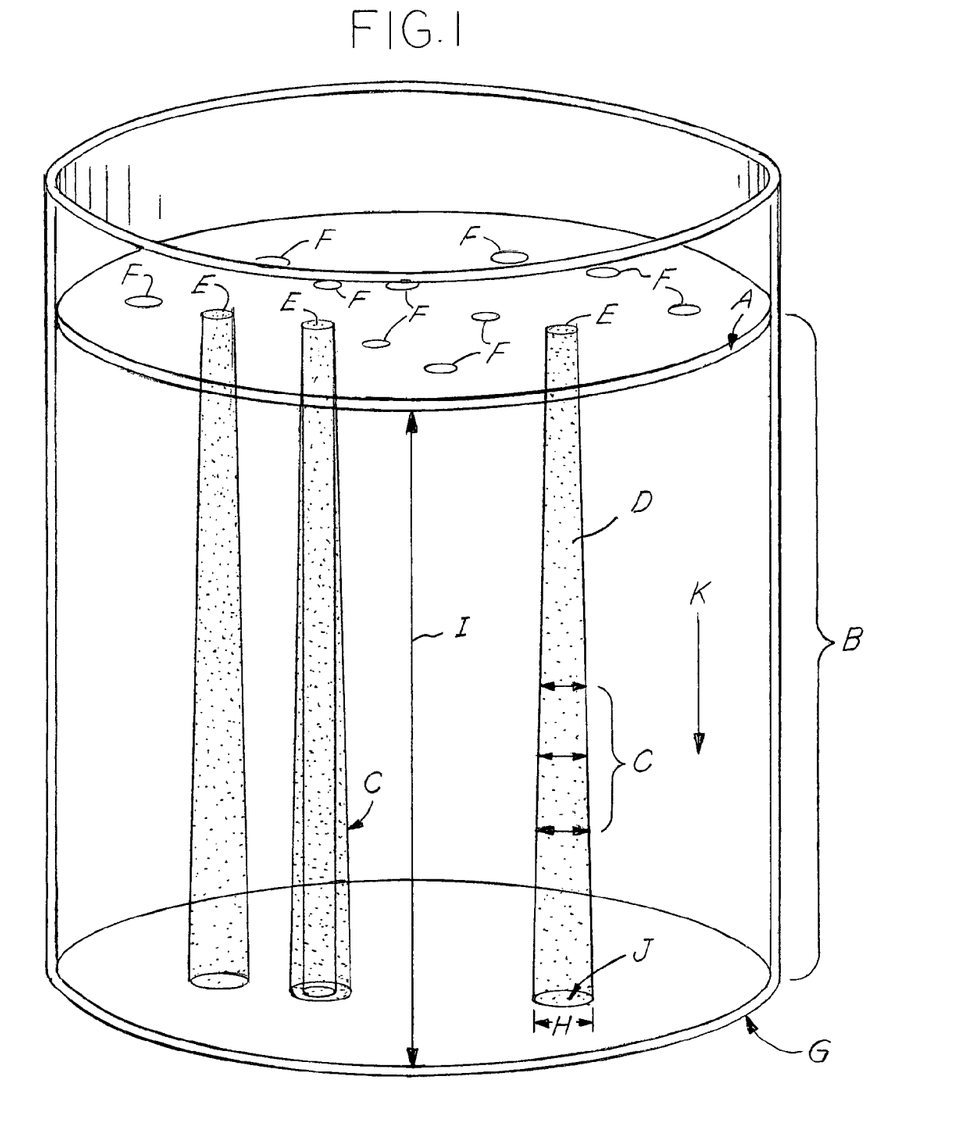
FIG. 1 is diagrammatic view of a test container used in this invention.

Drawing 1 shows the physics of the new method, not drawn to scale. It depicts an open container with bacteria growing on a surface. A represents a membrane filter, if present. B is an absorbent pad or gel or both. A and B constitute the base in this case. C represents lateral diffusion of soluble fluorophore or chromophore molecules as forces (wicking, absorbency) urge them to the bottom of the petri dish through the pad. D represents a soluble fluorophore or chromophore molecule. E represents *E. coli*, fluorescing under UV/black light because of the soluble fluorophore(s). It may be visible because of soluble or insoluble chromophore(s). F represents bacteria that do not produce the soluble fluorophore(s) and/or soluble chromophore(s) since they do not have the proper enzyme. Both E and F may fluoresce or be visible on the surface at the top due to substrate(s) that release insoluble chromophore(s) and/or insoluble fluorophore(s). The bottom of the container is G. H is the width of the fluorescent spot as seen through the bottom of the dish, and may be represented in the drawing as wider than actual for purposes of this explanation. I is the thickness of the absorbent pad or gel or both. J is the fluorescent spot as seen through the bottom of the dish, as soon as it is visible at any point during its travel through the pad or gel or both, as when it finally reaches the bottom of the pad or gel or both. K is a force urging the fluorophores/chromophores downward through the pad. The lesser the value of I, the thinner the absorbent pad will be, and the less distance the fluorophore/chromophore has to travel, and the sooner J will be seen and the less C will occur and the less H will be (smaller spot) and the sooner the test results will be detectable. D must be soluble at least to a moderate degree for this to occur.

As mentioned earlier, this invention also relates particularly to the detection of entities through the use of a newly defined group of enzyme substrates which we will be referenced as dual enzyme substrates. They are characterized by their ability to express enzymatic activity both in the production of a colored product (chromophore) visible in ambient daylight and in the production of a fluorescent product (fluorophore) visible under long wave UV radiation. These products may be present simultaneously or at separate time intervals during the enzyme activity period. Until the present discovery of this novel property of dual activity, it was generally assumed and accepted that diagnostic enzyme substrates may produce either fluorescent or chromogenic, or non-fluorescent or non-chromogenic products; however, none has been described as producing both fluorescent and chromogenic properties, both of which are useful in diagnostic applications.

Dual enzyme substrates may be used to great advantage alone or in combination with other substrates which are exclusively fluorescent or chromogenic or non-chromogenic in nature.

The prototypic dual enzyme substrate which was involved in the initiation of this invention is 6-chloro-3-indolyl-β-D-galactoside (Red Gal®) which was first synthesized and used, as previously described in this text. The fact that it and related compounds contain the unique dual capacity has not been either recognized or utilized until the advent of this invention. Although Red Gal® will be used for illustrative purposed concerning applications and novel uses in this discussion, it is not meant to limit the scope of related compounds sharing this dual nature.

Prior to this invention, Red Gal® has been widely used as a chromogenic enzyme substrate in diagnostic media to identify entities based upon the production of a red/pink insoluble product upon cleavage by the enzyme galactosidase. No note has ever been taken of any possible fluorescent product production which may be useful in the diagnostic process.

The following are examples of the use for dual substrates:

Basal Medium

A nutrient medium consisting of the following ingredients:
 a. peptone
 b. yeast extract
 c. dipotassium phosphate
 d. sodium chloride
 e. selective inhibitors (optional—may include antibiotics, bile salts or related compounds)
 f. gelling agent (optional—may include agar, pectin, alginate, or other gums)
 g. deionized or distilled water
 h. buffer material Example 1

The Basal Medium+6-chloro-3-indolyl-beta-D-glucuronide (Red Gluc);
 a. Basal Medium plus Red Gluc is added to saturate a thin pad covering the bottom of a small petri dish;
 b. An aqueous sample containing entities to be quantified and identified (in this case *E. coli* and other coliform bacteria) is filtered through a micropore filter which is then transferred (top side up) to rest on the surface of the thin pad;

c. This inoculated dish is then incubated at 35° C.;

d. At 12-14 hrs incubation the dish should be opened and the open side of the dish placed under a long wave UV (3540 Å) in the dark and observed (preferably with 10× magnification);

e. Colony forming units of *E. coli* will glow a bright blue fluorescent color. When the dish is observed in ambient (non-UV) light, there will likely be no apparent colonies visible. Observation of the underside of the disc under UV light indicates no fluorescence and therefore no soluble fluorophore production;

f. Replace the lid and return the dish to the incubator until 22-26 hrs have lapsed and repeat the observation process. At this time under the UV, there will be little or no observable fluorescence, but under ambient light, the *E. coli* colonies (which showed only as fluorescent spots earlier) will be visible as red/pink dots.

Example 2

The Basal Medium+Red Gluc+5-bromo-4-chloro-3-indolyl-beta-D-galactoside (X-Gal);

a. Basal Medium plus Red Gluc and X-Gal is added to saturate a thin pad covering the bottom of a small petri dish;

b. An aqueous sample containing entities to be quantified and identified (in this case *E. coli* and other coliform bacteria) is filtered through a micropore filter which is then transferred (top side up) to rest on the surface of the thin pad;

c. This inoculated dish is then incubated at 35° C.;

d. At 12-14 hrs incubation the dish should be opened and the open side of the dish placed under a long wave UV (3540 Å) in the dark and observed (preferably with 10× magnification);

e. The dish will appear as described in step e of Example 1 above;

f. Replace the lid and return the dish to the incubator until 22-26 hours have lapsed and repeat the observation process. At this time there will be little or no observable fluorescence, but under ambient light, the *E. coli* colonies will be visible as dark blue/purple dots and the other coliform colonies will be visible as green (teal) dots.

Example 3

The Basal Medium+5-bromo-4-chloro-3-indolyl-beta-D-galatoside(X-Gluc)+Red Gal+MU Gluc a. Basal Medium plus X-Gluc, Red Gal, and MU Gluc is added to saturate a thin pad covering the bottom of a small petri dish;

b. An aqueous sample containing entities to be quantified and identified (in this case *E. coli* and other coliform bacteria) is filtered through a micropore filter which is then transferred (top side up) to rest on the surface of the thin pad;

c. This inoculated dish is then incubated at 35° C.;

d. Invert the dish and place it under a UV light. You will observe bright blue fluorescent spots representing each colony forming unit of *E. coli*. These spots are caused by the soluble product from the MU Gluc which have diffused through the medium-saturated pad;

e. Now turn the dish right side up, remove the lid and place it under the UV light. You will observe fluorescent blue spots representing the total coliform population (including the *E. coli*). This fluorescence is a combination of the insoluble product of the Red Gal (affecting all the coliforms, including the *E. coli*) and the soluble product of the MU Gluc (affecting only the *E. coli*). The colonies themselves may or may not be visible, the likelihood being that the *E. coli* colonies may show as very tiny, pale blue dots, with the other coliforms not yet visible;

f. Replace the lid and return the dish to incubate until a total of 22-26 hrs lapse and reexamine the dish. At this time, the fluorescent spots on the underside of the dish (representing *E. coli* colonies) will be considerably larger and may have overlapped each other, depending upon how close the colonies are in proximity to one another. However, it is to be noted the fluorescence persists;

g. Upon turning the dish right side up and examining, it will be noted that under the UV, the previously fluorescent non-*E. coli* coliform colonies have lost their fluorescence, but the *E. coli* retain fluorescence and it has spread significantly. Also, in ambient room light, the non-*E. coli* coliform colonies are now visible as red/pink dots, while the *E. coli* colonies are a dark blue/purple color;

There is a fundamental difference in expression and existence between the soluble fluorophores of standard fluorogenic compounds and the insoluble fluorophores of the dual enzyme fluorogenic compounds. The soluble fluorophores, upon formation, persist in the environment and continue to diffuse or spread throughout the surrounding test area from the point of origin. They do not remain confined within the entity in which they were produced. The insoluble fluorophores, upon formation, exist or persist only as long as they do not complex with each other or any other chemical entity; usually a period not generally longer than 24 hours, and do not diffuse from their point of origin. They remain confined within the entity where they were produced.

Currently known dual enzyme substrates are members of the Chromogenic Indolyl based enzyme substrate. Their functional characteristics are not limited to this specific group of compounds. The prototypic dual enzyme substrate used in the aforementioned examples was 6-chloro-3-indolyl-beta-D-galactoside and it was found that the insoluble fluorescence was due to the side chain on the indolyl at the #6 position. Thus any halogen (fluorine, chlorine, bromine, iodine) may be used. Therefore, a wide range of substrates may be synthesized with a dual enzyme capability.

The invention is not to be limited to the details above given but may be modified in accordance with the following claims.

We claim:

1. A method of detecting target organisms comprising the steps:
   a. obtaining a sample which may contain said specific target organisms;
   b. adding at least one chromogenic or fluorogenic diagnostic material to a medium and to an absorbent device which can absorb said medium with said absorbent device, wherein said device serves as a base;
   c. contacting said sample with said material at one side of said absorbent device to cause upon incubation an enzyme reaction whereby an enzyme is produced by target organisms if said target organisms are present, some products derived from said enzyme reaction being visible and at least one of said products being diffusible in water; and
   d. viewing said one side and the opposite side of said absorbent device and detecting any fluorescent product appearance representing said specific target organisms and/or any chromogenic product appearance representing said specific target organisms, while said organisms are in contact with said diagnostic material.

2. A method of detecting target organisms comprising the steps:
   a. obtaining a sample which may contain entities including said target organisms;
   b. adding to an absorbent base a diagnostic material comprising a dual enzyme substrate that is both fluorogenic and chromogenic;
   c. contacting said sample with said material to cause upon incubation an enzyme reaction whereby an enzyme is produced by said target organisms and at least one product derived from said enzyme reaction is visible; and
   d. viewing said base with both a UV light to detect any fluorescent product appearance and a visible light to detect any chromophoric product appearance for the same target organism while said organisms are in contact with said diagnostic material.

3. The method of claim 1, wherein said absorbent device is an absorbent pad.

4. The method of claim 1, wherein UV light is used to detect said fluorescent product appearance and visible light is used to detect said chromogenic product appearance.

5. The method of claim 1, wherein said material includes at least one of a coumarin based fluorogen, a naphthyl based fluorogen, a fluorescein based fluorogen, a nitrophenyl based substrate, or a methylumbelliferyl based fluorogen.

6. The method of claim wherein said target organism includes microorganisms.

7. The method of claim 1, wherein said medium may be a solid, a gel, or a liquid.

8. The method of claim 1, wherein the sample is first passed through a membrane and said target organisms are retained on one side of a membrane, an opposite side of said membrane contacting said base.

9. The method of claim 2, wherein said material is an indolyl based enzyme substrate.

10. The method of claim 9, wherein said enzyme substrate is a 6-halogen-3-indolyl based enzyme substrate.

11. The method of claim 2, wherein the sample is first passed through a membrane and said target organisms are retained on one side of a membrane, an opposite side of said membrane contacting said base.

12. The method of claim 2, wherein said fluorescent product appearance remains in the vicinity of the target organisms for the duration of said appearance.

* * * * *

UNITED STATES PATENT AND TRADEMARK OFFICE
CERTIFICATE OF CORRECTION

| | | |
|---|---|---|
| PATENT NO. | : 8,008,059 B1 | Page 1 of 1 |
| APPLICATION NO. | : 11/725088 | |
| DATED | : August 30, 2011 | |
| INVENTOR(S) | : Geoffrey N. Roth and Jonathan N. Roth | |

It is certified that error appears in the above-identified patent and that said Letters Patent is hereby corrected as shown below:

In Claim 6, line 1, following the word "claim" add -- 1, --.

Signed and Sealed this
Eighteenth Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,008,059 B1 | Page 1 of 1 |
| APPLICATION NO. | : 11/725088 | |
| DATED | : August 30, 2011 | |
| INVENTOR(S) | : Geoffrey N. Roth and Jonathan N. Roth | |

It is certified that error appears in the above-identified patent and that said Letters Patent is hereby corrected as shown below:

Column 10, line 3 (Claim 6, line 1) following the word "claim" add -- 1, --.

This certificate supersedes the Certificate of Correction issued October 18, 2011.

Signed and Sealed this
Twenty-second Day of November, 2011

David J. Kappos
*Director of the United States Patent and Trademark Office*